United States Patent [19]

Schweizer

[11] Patent Number: 5,166,202
[45] Date of Patent: Nov. 24, 1992

[54] METHOD FOR THE TREATMENT OF PANIC DISORDER

[75] Inventor: Edward E. Schweizer, Wilmington, Del.

[73] Assignee: Trustees of the University of Pennsylvania, Philadelphia, Pa.

[21] Appl. No.: 809,205

[22] Filed: Dec. 13, 1991

Related U.S. Application Data

[63] Continuation of Ser. No. 584,761, Sep. 19, 1990, abandoned.

[51] Int. Cl.$^5$ ............................................. A01N 43/62
[52] U.S. Cl. ..................................... 514/220; 514/219
[58] Field of Search ................................ 514/219, 220

[56] References Cited

U.S. PATENT DOCUMENTS 4,950,664  8/1990  Goldberg .......................... 514/219

OTHER PUBLICATIONS

Ballenger, J. C. et al., "Alprazolam in panic disorder and agoraphobia: results from a multicenter trial. I. Efficacy in short-term treatment," *Arch Gen Psychiatry*, 45:413-422 (1988).

Wheeler, E. O., et al., "Neurocirculatory asthenia: a 20-year follow-up study of 173 patients," *JAMA*, 142:878-889 (1950).

Breier A. et al., "Agoraphobia with panic attacks: development, diagnostic stability, and course of illness," *Arch Gen. Psychiatry*, 43:1029-1036 (1986).

Noyes, R. et al., "Problems with tricyclic antidepressant use in patients with panic disorder or agoraphobia: results of a naturalistic follow-up study," *J. Clin. Psychiatry*, 50163-169 (1989).

Nagy, L. M. et al., "Clinical and medication outcome after short-term alprazolam and behavioral group treatment in panic disorder," *Arch Gen Psychiatry*, 46:993-999 (1989).

Noyes, R. et al., "Follow-up study of patients with panic disorder and agoraphobia with panic attacks treated with tricyclic antidepressants," *J. Affective Disord*, 16:249-257 (1989).

Mavissakalian, M. et al., "Imipramine in the treatment of agoraphobia: dose-response relationships," *Am J. Psychiatry*, 142:1032-1036 (1985).

Rickels, K. et al., "Chronic therapeutic use of benzodiazepines: I. Effects of abrupt discontinuation," *Arch Gen Psychiatry* (in press).

Schweizer, E. et al., "Chronic therapeutic use of benzodiazepines: II. Effects of gradual taper," *Arch Gen. Psychiatry* (in press).

Roy-Byrne, P. P. et al., "Benzodiazepine withdrawal: overview and implications for the treatment of anxiety." *Am J. Med.*, 84:1041-1052 (1988).

Reves, J. G. et al., "Midazolam" pharmacology and uses, *Anesthesiology*, 62:310-324 (1985).

Dundee, J. W. et al., "Midazolam" a review of its pharmacological properties and therapeutic use, *Drugs*, 28:519-541 (1984).

Forrest, P. et al., "Placebo controlled comparison of midazolam, triazolam and diazepam as oral premedicants for outpatient anaesthesia," *Anaesth Intens Care*, 15:296-304 (1987).

O'Boyle, C. A. et al., "Comparison of midazolam by mouth and diazepam IV in outpatient oral surgery," *Br J. Anaesth*, 59:746-754 (1987).

Hargreaves, J., "Benzodiazepine premedication in minor day-case surgery: comparison of oral midazolam and temazepam with placebo," *Br J. Anaesth*, 61:611-616 (1988).

Clausen, T. G., et al., "Pharmacokinetics of midazolam and alpha-hydroxy-midazolam following rectal and intravenous administration," *Br J. Clin. Pharmacol*, 25:457-463 (1988).

Wilton, N. C. T. et al., "Preanesthetic sedation of preschool children using intranasal midazolam," *Anesthesiology*, 69:972-975 (1988).

Noyes, R. et al., "Alprazolam in panic disorder and agoraphobia: Results from a multicenter trial. II. Patient acceptance, side effects, and safety," *Arch Gen Psychiatry*, 45:423-428 (1988).

Greenblatt, D. J. et al., "Pharmacokinetic and electroencephalographic study of intravenous diazepam, midazolam, and placebo," *Clin. Pharmacol Ther*, 45:356-365 (1989).

Sostmann, H. J. et al., "Dose equivalence of midazolam and triazolam," *Eur J. Clin Pharmacol*, 36:181-187 (1989).

Forster A., "Respiratory depressant effects of different doses of midazolam and lack of reversal with naloxone-a double-blind randomized study", *Anesth Analg*, 62:920-924 (1983).

Curtis, L. D. et al., "Arterial oxygen desaturation following intravenous injection of midazolam," *J Amer Assoc of Nurse Anesth*, 57:244-249 (1989).

Rickels, K. et al., "Long-term diazepam therapy and clinical outcome," *JAMA*, 250:767-771 (1983).

Rickels, K. et al., "Long-term treatment of anxiety and risk of withdrawal. Prospective comparison of clorazepate and buspirone," *Arch Gen Psychiatry*, 45:444-450 (1988).

(List continued on next page.)

Primary Examiner—Frederick E. Waddell
Assistant Examiner—T. J. Criares
Attorney, Agent, or Firm—Woodcock Washburn Kurtz Mackiewicz & Norris

[57] ABSTRACT

Midazolam and its pharmaceutically acceptable salts are useful in the treatment of panic disorder, panic attacks and the prevention of panic attacks.

6 Claims, No Drawings

OTHER PUBLICATIONS

Allen, R. P. et al., "Efficacy without tolerance or rebound insomnia for midazolam and temazepam after use for one to three months," *J Clin Pharmacol,* 25:457–463 (1987).

Koopmans, R. et al., "Pharmacokinetic–pharmacodynamic modeling of midazolam effects on the human central nervous system," *Clin Pharmacol Ther,* 44:14–22 (1988).

Schweizer, E. et al., "Lorazepam vs. alprazolam in the treatment of panic disorder," *Pharmacopsychiatry,* 23:90–93 (1990).

de Wit, H. et al., "Lack of preference for diazepam in anxious volunteers," *Arch Gen Psychiatry,* 43:533–541 (1986).

Ciraulo, D. A. et al., "Parental alcoholism as a risk factor in benzodiazepine abuse: a pilot study," *Am J Psychiatry,* 146:1333–1335 (1989).

METHOD FOR THE TREATMENT OF PANIC DISORDER

This is a continuation of application Ser. No. 584,761, filed Sep. 19, 1990, now abandoned.

FIELD OF THE INVENTION

This invention relates to a method for treatment of panic disorder. More particularly, a method of treating panic disorder with intranasal midazolam is provided.

BACKGROUND OF THE INVENTION

Panic disorder is an illness which is estimated to afflict 1.5-2% of the adult population. The hallmark of panic disorder is the sudden, crescendo panic attack which may be as fleeting as a few minutes in duration, or may persist for over an hour before subsiding. The majority of patients suffering from panic disorder report an average attack frequency (four 4-symptom attacks) of less than one per day, which is true even for many moderate-to-severely ill patients such as those treated in the large Cross-National Collaborative Panic Study (Ballenger, J. C. et al., "Alprazolam in panic disorder and agoraphobia: results from a multicenter trial. I. Efficacy in short-term treatment," *Arch Gen Psychiatry*, 45:413-422 (1988)).

Current treatment strategies for panic disorder focus on attempts to control and prevent these intermittent, but severe and often disabling panic attacks, and thereby to reduce the associated inter-episode anticipatory anxiety, phobic avoidance, and somatic preoccupations. To accomplish this effectively with drug therapy requires daily doses of high potency benzodiazepines such as alprazolam, or daily doses of antidepressants such as imipramine.

Due to the chronicity of panic disorder, (Wheeler, E. O. et al., "Neurocirculatory asthenia: a 20-year follow-up study of 173 patients," *JAMA*, 142:878-889 (1950); Coryell, W. et al., "Panic disorder and primary unipolar depression: a comparison of background and outcome," *J Affective Disorders*, 5:311-317 (1983); Breier A. et al., "Agoraphobia with panic attacks: development, diagnostic stability, and course of illness," *Arch Gen. Psychiatry*, 43:1029-1036 (1986)) many patients require treatment for many months or years, and still frequently relapse upon drug discontinuation (Noyes R. et al., "Problems with tricyclic antidepressant use in patients with panic disorder or agoraphobia: results of a naturalistic follow-up study," *J. Clin. Psychiatry*, 50163-169 (1989); Nagy, L. M. et al., "Clinical and medication outcome after short-term alprazolam and behavioral group treatment in panic disorder," *Arch Gen Psychiatry*, 46:993-999 (1989); Schweizer, E. et al., "Clinical and medication status at one-year follow-up after maintenance treatment of panic disorder," Presented at CINP Congress, Munich, August 1988).

Though drug therapy for panic disorder is generally highly effective, many patients cannot tolerate antidepressant therapy (Noyes, R. et al., "Follow-up study of patients with panic disorder and agoraphobia with panic attacks treated with tricyclic antidepressants," *J. Affective Disord*, 16:249-257 (1989); Mavissakalian, M. et al., "Imipramine in the treatment of agoraphobia: dose-response relationships," *Am J. Psychiatry*, 142:1032-1036 (1985)). Similarly, the risk of physical dependence and a withdrawal reaction upon drug discontinuation deters many patients from optimal use of the benzodiazepines for the treatment of panic disorder which can be severely disabling, but intermittent in nature. (Rickels, K. et al., "Chronic therapeutic use of benzodiazepines: I. Effects of abrupt discontinuation," *Arch Gen Psychiatry* (in press); Schweizer, E. et al., "Chronic therapeutic use of benzodiazepines: II. Effects of gradual taper," *Arch Gen. Psychiatry* (in press); Roy-Byrne, P. P. et al., "Benzodiazepine withdrawal: overview and implications for the treatment of anxiety," *Am J. Med.*, 84:1041-1052 (1988))

SUMMARY OF THE INVENTION

There is provided by this invention a novel method for the treatment of panic disorder comprising the nasal administration of an effective amount of midazolam in a pharmaceutically acceptable nasal carrier to a mammal in need of such treatment.

Further provided by this invention is a novel method for the treatment of panic attacks comprising the nasal administration of an effective amount of midazolam in a pharmaceutically acceptable nasal carrier to a mammal in need of such treatment.

Further provided by this invention is a method for the prevention of panic attacks comprising the nasal administration of an effective amount of midazolam in a pharmaceutically acceptable nasal carrier to a mammal in need of such treatment.

Applicant has recognized that the rapid onset of action of midazolam administered by this novel route would not only reduce overall panic attack frequency and reduce interepisode levels of non-panic anxiety, but would also control incipient panic attacks.

DETAILED DESCRIPTION OF THE INVENTION

The method of this invention is useful in treating panic disorder. The American Psychiatric Association defines Panic Disorder as the repeated occurrence over at least a 4 week period of sudden panic attacks characterized by at least 4 of the following symptoms: dyspnea, dizziness, tachycardia or palpitations, tremulousness, sweating, choking, nausea or abdominal distress, depersonalization or derealization, numbness or tingling, hot flushes or chills, chest pain or discomfort, fear of dying, fear of going crazy or losing control. See, American Psychiatric Association, "Diagnostic and Statistical Manual of Mental Disorders," Third Edition, Revised, Washington, D.C., American Psychiatric Association, (1987).

The method of this invention is useful in treating panic attacks. Panic attacks are sudden episodes of intense fear or discomfort associated with any one of the above-listed symptoms, though most commonly palpitations or tachycardia, tremulousness, sweating or hot flushes. The panic attack can occur spontaneously, though more commonly they are triggered by a feared situation, e.g. elevators, planes, talking or performing in front of a group.

The method of this invention is further useful in the prevention of panic attacks. For example, when confronted with situations known or suspected of triggering a panic attack, the patient can be treated in accordance with the invention.

8-chloro-6-(2-fluorophenyl)-1-methyl-4H-imidazo[1,5-a][1,4]benzodiazepine, or midazolam, is intended for use in the present invention. Midazolam is available in the USA as the hydrochloride salt for parenteral (intravenous) injection (sold under the trademark Versed ® by Roche Products Inc., Manati, Puerto Rico) as a premedicant prior to surgery (Reves, J. G. et al., "Midazolam: pharmacology and uses," *Anesthesiology*, 62:310–324 (1985)). The current indications for use for midazolam are: 1) For preoperative sedation and to impair the memory of perioperative events, 2) As an agent for conscious sedation during outpatient surgery or other procedures, and 3) For administration with other anesthetic agents for the induction of general anesthesia.

The ability to form a salt, conferred by virtue of the imidazole ring, results in midazolam being readily soluble in water at pH 4, and thus suitable for intranasal administration. Upon entering the bloodstream, the physiologic pH converts midazolam into the most highly lipophilic of all available benzodiazepines, resulting in rapid entry in the CNS, and an onset of clinical effect which is measured in minutes (Dundee, J. W. et al., "Midazolam: a review of its pharmacological properties and therapeutic use," *Drugs*, 28:519–541 (1984)). In addition, the intranasal route of administration avoids the so-called "first-pass" effect whereby orally or intravenously administered midazolam is first circulated through the liver, where more than 50% of it is metabolically inactivated. As a result, a larger proportion of midazolam can reach the CNS where it is active.

Midazolam has an elimination half-life of approximately 2–3 hours (Reves, J. G. et al., supra and Dundee, J. W. et al., supra), and it has been found to have a significantly faster offset of action than triazolam (Forrest, P. et al., "Placebo controlled comparison of midazolam, triazolam and diazepam as oral premedicants for outpatient anaesthesia," *Anaesth Intens Care*, 15:296–304 (1987)).

Besides IV use, there have been reports of midazolam being administered safely and effectively by oral (Forrest, P. et al., supra; O'Boyle, C. A. et al., "Comparison of midazolam by moth and diazepam IV in outpatient oral surgery," *Br J. Anaesth*, 59:746–754 (1987); Hargreaves, J., "Benzodiazepine premedication in minor daycase surgery: comparison or oral midazolam and temazepam with placebo," *Br J. Anaesth*, 61:611–616 (1988)), rectal (Saint-Maurice, C. et al., "The pharmacokinetics of rectal midazolam for premedication in children," *Anesthesiology*, 65:536–538 (1986); Clausen T. G., et al., "Pharmacokinetics of midazolam and alpha-hydroxy-midazolam following rectal and intravenous administration," *Br J. Clin. Pharmacol*, 25:457–463 (1988)), and intranasal (Wilton, N. C. T. et al., "Preanesthetic sedation of preschool children using intranasal midazolam," *Anesthesiology*, 69:972–975 (1988)) routes prior to surgery. In the latter report, intranasal midazolam in doses of 0.2–0.3 mg/kg were employed to achieve conscious sedation in children, ages 18 months to 5 years, who were undergoing surgery.

The route of administration of midazolam in the method of this invention is intranasal. Pharmaceutically acceptable nasal carriers suitable for use in the present invention are known. Examples include saline solutions, alcohols, glycols, glycolethers and mixtures thereof. "Remington's Pharmaceutical Sciences," 14th Edition, (1970). The choice of a suitable carrier for the method of the present invention will generally depend on the particular nasal dosage form. For example, midazolam may be formulated into a nasal solution for use as drops or as a spray, a nasal suspension, a nasal ointment and a nasal gel. For ease of administration, a nasal spray is expected to be the preferred form of administration.

The effective dosage of midazolam for the treatment of panic disorder depends on the age, weight and condition of the patient. The effective dosage is expected to be a lesser amount of midazolam, preferably from about one-half to about one-fifteenth, than the dosage of midazolam employed for IV administration for sedation and anesthesia. Generally, for adults a dosage range of from about 0.25 mg to about 5 mg per day in a single or divided dose is expected to be effective in the treatment of panic disorder, panic attacks, and the prevention of panic attacks.

EXAMPLE

Method

Patients in this example met DSM III-R criteria for panic disorder, either uncomplicated, with limited phobic avoidance, or with agoraphobia. American Psychiatric Association, "Diagnostic and Statistical Manual of Mental Disorders," Third Edition, Revised, Washington, D.C., American psychiatric Association, (1987). Patients were excluded who had a history in the past year of major depression or alcoholism, or who had any history of drug abuse, bipolar disorder, schizophrenia, seizures, or organic mental disorders. No psychotropic medication was permitted for 2 weeks prior to the screen evaluation. All patients provided written informed consent. The study was approved by an institutional review board.

This Example had a double-blind, crossover design consisting of 3 weeks of treatment with intermittent or "as needed" does of intranasal midazolam and 3 weeks of intranasal normal saline. Patients were randomly assigned as to the order of treatment. All patients underwent a semi-structured psychiatric evaluation using DSM III-R diagnostic checklists to evaluate the presence or absence of comorbid Axis I diagnoses. Patients reporting 1 or more major panic attacks ($>4$ symptoms) in each of the 3 previous weeks were prospectively followed for one week off medication.

Midazolam was dispensed as an aqueous solution of the hydrochloride, which is clear, almost colorless, and is stable for up to 2 years at room temperature. It was stored in glass dropper bottles and patients were instructed to lean their head back and administer 1–4 drops as needed at the earliest onset of a panic attack. For patients administering 3–4 drops, 1–2 drops were placed in each nostril. One drop delivered 0.05 ml, which contained 0.25 mg of midazolam. Patients were told to keep their head tilted back for approximately 30 seconds to allow for absorption. They were cautioned about driving or engaging in other activities which might be risky during the ensuing 2 hours.

Patients were sent home with a panic diary and asked to record the frequency of major panic attacks, defined as sudden surges of anxiety which were associated with 4 or more symptoms from the DSM III-R diagnostic checklist. They were also asked to record the intensity of each attack on a 1 to 10 severity scale. Finally, they were asked to note the frequency and timing of each of their doses of study drug.

Patients were seen for weekly visits: at screen, at baseline, and at weeks 1–6 on study drug. At each visit, patients were queried for adverse effects using a standardized 42-item Symptoms and Side Effects Inventory (Noyes, R. et al., "Alprazolam in panic disorder and agoraphobia: Results form a multicenter trial. II. Patient acceptance, side effects, and safety," *Arch Gen Psychia-* try, 45:423-428 (1988)). They also completed an 11-point global phobia scale which rate severity on a scale from 0-none to 10-severe (Ballenger, J. C., et al., supra); and the Sheehan patient-rated anxiety scale (SPRAS), a 40-item self-rated questionnaire which quantifies panic anxiety symptomatology on a 0-4 severity scale (Sheehan, D. V. et al., "Some biochemical correlates of panic attacks with agoraphobia and their response to a new treatment," *J. Clin. Psychoparmacol*, 4(suppl 2):66-75 (1984)). Patients were evaluated by the study physician using the standard Hamilton anxiety (HAM-A) and 7-point clinical global improvement (CGI) scales. The study physician also totalled up the weekly panic attacks using the patient diary as a guide, discussing any unclear information with the patient at the time of the visit.

Five patients were enrolled in this preliminary pilot study who were seeking private psychiatric treatment for panic anxiety but were offered free participation in the study as an alternative. Table 1 summarizes relevant demographic and clinical information on the patients. Patient #1 reported an episode of major depression more than 2 years prior to study entry. Patient #4 had comorbid diagnoses of social phobia and agoraphobia, and was unemployed due to this illness, which had resulted in significant disability. Patient #5 reported a history of alcoholism, but had been abstinent for more than 3 years prior to study entry.

TABLE 1

Summary of Demographic and Clinical Information

| | Patient | | | | |
|---|---|---|---|---|---|
| | #1 | #2 | #3 | #4 | #5 |
| Age | 37 | 36 | 40 | 30 | 32 |
| Sex | F | F | M | M | M |
| Diagnosis | P.D., L. | P.D., U. | P.D., L. | A. | P.D., L. |
| Age of onset | 31 | 24 | 30 | 22 | 26 |
| Previous Rx | TCA Benzo | Benzo | Benzo | None | Benzo |

P.D. - Panic disorder
L. - limited phobic avoidance
U. - uncomplicated
A. - agoraphob. soc. phobia
TCA - tricyclic antidepressant
Benzo - benzodiazepine

Results

Table 2 summarizes the clinical measures obtained on each patient during the course of the study. Patients #1-3 received midazolam for 3 weeks before being blindly switched to placebo. Patients #4 and #5 received placebo first before being blindly switched to midazolam. Patient #5 reported such severe panic anxiety for 2 weeks on placebo that the decision was made to advance him to the other blinded medication (midazolam) one week early.

As can be seen from Table 2, three patients (#1, #3, #5) were "much"—2, or "very much"—1, improved at the end of 3 weeks of midazolam. All three reported complete blockade of panic attacks by the third week. One patient (#2) had more modest, but still clear-cut improvement in reported panic attacks. Patient #4 was also assessed by the study physician as having had some minimal improvement on the CGI, but this was not reflected in consistent improvements in either number of weekly panic attacks or in reductions in the HAM-A or the SPRAS.

For the four improved patients, control of panic attacks was accompanied by significant reductions both in panic anxiety symptomatology as measured by the SPRAS, and in the overall level of generalized, non-panic anxiety as measured by the HAM-A. For the three much improved patients (#1, #3, #5), the 10-point global phobia scale improved, during the 3 weeks of midazolam therapy, from 3 to 1, from 5 to 4, and from 10 to 3, respectively. Patient #2 had no associated phobias, so no ratings were performed. Patient #4, who was unimproved, reported a 10 on the phobic avoidance scale for all visits.

All patients, except patient #4, self-administered 2 drops (0.5 mg) of midazolam at each dose. Patient #4 reported sedation and unsteadiness on his feet for approximately 30 minutes after taken 2 drops, so he reduced to 1 drop per dose, and the adverse effects subsided. The only other adverse effect, which was noted by 2 other patients, was a mild burning in the nose at the time of midazolam administration.

The average number of doses of midazolam administered per week by the study patients was as follows: For week #1—6.9 does; for week #2—6.5 doses; for week #3—6.1 doses. The highest number of weekly doses administered was 12, and the lowest was 3. Six doses represents a cumulative weekly dose of 3 mg of midazolam.

All 3 patients who received midazolam first sustained their clinical improvement after the blinded switch to placebo.

TABLE 2

Summary of Clinical Measures on Study Treatment

| | Base | | | Week | | | |
|---|---|---|---|---|---|---|---|
| | 0 | 1 | 2 | 3 | 4 | 5 | 6 |
| Patient #1 | Midazolam | | | Placebo | | | |
| # Panic Attacks | 4.5 | 1 | 0 | 0 | 0 | 0 | 0 |
| HAM-A | 21 | 5 | 5 | 6 | 1 | 1 | 2 |
| SPRAS | 67 | 22 | 13 | 8 | 2 | 3 | 2 |
| CGI | — | 2 | 1 | 1 | 1 | 1 | 1 |
| Patient #2 | | | | | | | |
| # Panic Attacks | 2.7 | 2 | 0 | 1 | 2 | 4 | 1 |
| HAM-A | 11 | 13 | 9 | 9 | 2 | 6 | 6 |
| SPRAS | 52 | 35 | 29 | 23 | 18 | 18 | 18 |
| CGI | — | 3 | 3 | 3 | 3 | 3 | 3 |
| Patient #3 | | | | | | | |
| # Panic Attacks | 6 | 11 | 0 | 0 | 0 | 0 | 1 |
| HAM-A | 15 | 8 | 5 | 3 | 8 | 9 | 13 |
| SPRAS | 21 | 16 | 11 | 9 | 18 | 22 | 29 |
| CGI | — | 2 | 2 | 1 | 2 | 3 | 3 |
| Patient #4 | Placebo | | | Midazolam | | | |
| # Panic Attacks | 2.5 | 7 | 6 | 6 | 2 | 3 | 6 |
| HAM-A | 29 | 24 | 21 | 20 | 22 | 20 | 22 |
| SPRAS | 90 | 83 | 68 | 65 | 53 | 67 | 78 |
| CGI | — | 4 | 4 | 4 | 3 | 3 | 3 |
| Patient #5 | | | | | | | |
| # Panic Attacks | 8 | 9 | 12 | — | 7 | 5 | 0 |
| HAM-A | 15 | 15 | 29 | — | 9 | 8 | 14 |
| SPRAS | 74 | 73 | 114 | — | 55 | 39 | 42 |
| CGI | — | 5 | 7 | — | 1 | 2 | 2 |

Low dose intranasal midazolam, administered on a targeted or "as needed" basis, is expected to be an effective treatment for panic disorder in many patients. Patients in this example generally reported either partial or complete suppression of the incipient panic attack for which they had administered midazolam, confirming the clinical relevance of the rapid onset of drug action by the intranasal route.

There was also clear evidence for a reduction in the frequency of panic attacks for the whole week. Of equal importance, levels of panic anxiety symptomatology, and of inter-episode generalized anxiety, both showed clear and persistent reductions. This anti-anxiety "halo effect" occurred despite the infrequency of the administration of midazolam, despite the short elimination half-life of the compound, and despite the low dose used. The elimination half-life of midazolam is estimated to be between 2 and 3 hours (Dundee, J. W. et al. supra). Given that patients averaged from 0 to 2 doses of midazolam per day, it was estimated that patients' plasma contained no measurable midazolam for at least 50% of any given treatment week.

The dose of midazolam employed in this example was 0.5 mg, which is relatively low. Dose equivalency studies suggest that 0.5 mg of midazolam is clinically comparable to approximately 2 mg of diazepam (Reves, J. G. et al. supra; Dundee, J. W. et al. supra; Greenblatt D. J., "Pharmacokinetic and electroencephalographic study of intravenous diazepam, midazolam and placebo," *Clin Pharmacol Ther,* 45:356-365 (1989); Sostmann, H. J. et al., "Dose equivalence of midazolam and triazolam," *Eur J. Clin Pharmacol,* 36:181-187 (1989).

In this example, the drug was generally well-tolerated and easily administered. Mild nasal burning was the only local side effect reported. Only one patient reported significant, though transient, sedation and psychomotor impairment.

The dose of midazolam employed here was well below (by approximately 10-fold) the minimal does required to produce clinically notable effects on ventilatory mechanics and arterial oxygen saturation (Reves, J. G. et al. supra; Dundee, J. W. et al. supra; Forster A., "Respiratory depressant effects of different doses of midazolam and lack of reversal with naloxone—a double-blind randomized study," *Anesth Analg,* 62:920-924 (1983); Curtis, L. D. et al., "Arterial oxygen desaturation following intravenous injection of midazolam," *J Amer Assoc of Nurse Anesth,* 57:244-249 (1989)).

No rebound effects were observed, either after single doses, or after discontinuing 3 weeks of targeted treatment. No tendency for tolerance to develop to the therapeutic effect was observed.

Finally, none of the patients reported euphoric effects from midazolam administration, and there was no trend for increasing dosing from week 1 to week 3. This is consistent with previous research on the long-term use of oral benzodiazepines to treat both generalized and panic anxiety, where escalations in dose are infrequently observed (Schweizer, E. et al., suora: Rickels, K. et al., "Long-term diazepam therapy and clinical outcome," *JAMA,* 250:767-771 (1983); Rickels, K. et al., "Long-term treatment of anxiety and risk of withdrawal. Prospective comparison of clorazepate and buspirone," *Arch Gen Psychiatry,* 45:444-450 (1988)). When they do occur, they usually signify intercurrent illness (e.g., depression) which requires antidepressant or other therapy.

I claim:

1. A method for treating a mammal suffering from panic disorder comprising administering nasally from about 0.5 mg to about 2 mg of midazolam in a pharmaceutically acceptable salt carrier at the onset of or during a panic attack.

2. The method of claim 1 wherein said midazolam is administered in amounts of from about 0.2 mg to about 0.6 mg per episode of panic attack.

3. The method of claim 1 wherein said midazolam is administered in amounts of from about 0.5 mg to about 1.5 mg per episode of panic attack.

4. A method of treating a mammal suffering from at least four of the symptoms of panic disorder selected from the group consisting of dyspnea, dizziness, tachycardia, heart palpitations, tremulousness, sweating, choking, nausea, abdominal distress, depersonalization, derealization, numbness, tingling, hot flushes, chills, chest pain, chest discomfort, fear of dying, fear of going insane, and fear of losing mental control, comprising administering nasally from about 0.5 mg to about 2 mg of midazolam in a pharmaceutically acceptable nasal carrier at the onset of said symptoms.

5. The method of claim 4 wherein said midazolam is administered in amounts of from about 0.2 mg to about 0.6 mg.

6. The method of claim 4 wherein said midazolam is administered in amounts of from about 0.5 mg to about 1.5 mg.

* * * * *

UNITED STATES PATENT AND TRADEMARK OFFICE
CERTIFICATE OF CORRECTION

PATENT NO. : 5,166,202
DATED : November 24, 1992
INVENTOR(S) : Schweizer

Page 1 of 2

It is certified that error appears in the above-identified patent and that said Letters Patent is hereby corrected as shown below:

Title page, column 1 beneath "4,950,664  8/1990 Goldberg ........514/219" please insert --4,510,153  4/1985 Coleman et al. .......514/220  4,634,703  1/1987  Kurtz et al. ........514/252--.

Title page, column 2 Line 2 delete "uses, *Anesthesiology*" and insert therefor --uses," *Anesthesiology*--.

Title page, column 2 Line 4 delete "use, *Drugs*" and insert therefor --use," *Drugs*--.

Title page, page 2, column 2, Line 7 delete "Ciraulo," and insert therefor --Circaulo--.

Column 3, Line 38 delete "moth" and insert therefor --mouth--.

Column 4, Line 21 delete "psychiatric" and insert therefor --Psychiatric--.

Column 4, line 31 delete "does of" and insert therefor --doses of--.

Column 6, Line 20 delete "#1-6.9 does;" and insert therefor --#1-6.9 doses;--.

Column 7 Line 26 delete "minimal does" and insert therefor --minimal dose--.

Column 8 Line 4 delete "suora:" and insert therefor --supra;--.

UNITED STATES PATENT AND TRADEMARK OFFICE
CERTIFICATE OF CORRECTION

PATENT NO. : 5,166,202
DATED : November 24, 1992
INVENTOR(S) : Schweizer

It is certified that error appears in the above-identified patent and that said Letters Patent is hereby corrected as shown below:

Column 8 Line 13 delete "I claim:" and insert therefor -- Claims--.

Column 8, Line 17 delete "salt carrier" and insert therefor -- nasal carrier--.

Signed and Sealed this

Fourth Day of January, 1994

Attest:

BRUCE LEHMAN

Attesting Officer

Commissioner of Patents and Trademarks